US008668921B2

(12) United States Patent
Nakai et al.

(10) Patent No.: US 8,668,921 B2
(45) Date of Patent: Mar. 11, 2014

(54) LIPASE INHIBITORS

(75) Inventors: Masaaki Nakai, Minoo (JP); Yuko Fukui, Takatsuki (JP); Sumio Asami, Ibaraki (JP); Fumio Hashimoto, Kagoshima (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1286 days.

(21) Appl. No.: 11/631,507

(22) PCT Filed: Jul. 5, 2005

(86) PCT No.: PCT/JP2005/012401
§ 371 (c)(1),
(2), (4) Date: Jan. 4, 2007

(87) PCT Pub. No.: WO2006/004114
PCT Pub. Date: Jan. 12, 2006

(65) Prior Publication Data
US 2008/0317821 A1 Dec. 25, 2008

(30) Foreign Application Priority Data
Jul. 5, 2004 (JP) .................................. 2004-198342

(51) Int. Cl.
| A61K 31/353 | (2006.01) |
| A61P 1/00 | (2006.01) |
| A61K 31/7048 | (2006.01) |
| A61K 31/355 | (2006.01) |
| A61K 31/375 | (2006.01) |
| A61K 31/202 | (2006.01) |
| A61K 31/195 | (2006.01) |
| A61K 31/015 | (2006.01) |

(52) U.S. Cl.
USPC ............ 424/439; 514/453; 514/456; 514/27; 514/458; 514/474; 514/560; 514/561; 514/763; 424/729; 424/94.1; 424/766

(58) Field of Classification Search
USPC ......... 424/439, 729, 94.1, 766; 514/453, 456, 514/27, 458, 474, 560, 561, 763
See application file for complete search history.

(56) References Cited

U.S. PATENT DOCUMENTS

| 2002/0146400 A1* | 10/2002 | Cincotta ..................... 424/94.1 |
| 2002/0146472 A1* | 10/2002 | Chen et al. .................... 424/729 |
| 2004/0097432 A1* | 5/2004 | Roh-Schmidt et al. ......... 514/27 |
| 2007/0178175 A1* | 8/2007 | Matsubara et al. ........... 424/729 |

FOREIGN PATENT DOCUMENTS

| EP | 0 522 502 A1 | 1/1993 |
| JP | 60-11912 | 3/1985 |
| JP | 1-102022 | 4/1989 |
| JP | 3-219872 | 9/1991 |
| JP | 03-228664 A | 10/1991 |
| JP | 7-61927 | 3/1995 |
| JP | 8-259557 | 10/1996 |
| JP | 9-40689 | 2/1997 |
| JP | 9-291039 | 11/1997 |
| JP | 2000-226329 | 8/2000 |
| WO | 03/045328 A2 | 6/2003 |
| WO | WO 03/045328 | 6/2003 |

OTHER PUBLICATIONS

Hashimoto et al., Bioorganic & Medicinal Chemistry Letters, vol. 6, No. 6, 695-700, 1996.*
Hyperlipidemia: retrieved from internet: http://en.wikipedia.org/wiki/Hyperlipidemia. Retrieved on May 30, 2013.*
Lipid: retrieved from internet: http://en.wikipedia.org/wiki/Lipid. Retrieved on May 30, 2013.*
Theaflavin: retrieved from internet. Retrieved on http://en.wikipedia.org/wiki/Theaflavin.*
Moreno et al., "Inhibitory Effects of Grape Seed Extract on Lipases," Nutrition, 2003, vol. 19, pp. 876-879.
Yoshikawa et al., "*Salacia reticulata* and its Polyphenolic Constituents with Lipase Inhibitory and Lipolytic Activities Have Mild Anti-obesity Effects in Rats," Journal of Nutrition, 2002, vol. 132, pp. 1819-1824.
Han et al., "Anti-obesity action of oolong tea," Int. J. Obes., 1999, vol. 23, pp. 98-105.
Iwata et al., "Effects of Oolong Tea on Plasma Lipids and Lipoprotein Lipase Activity in Young Women," Nippon Eiyo Shokuryo Gakkaishi (J. Jpn. Soc. Nutr. Food Sci,) 1991, vol. 44, No. 4, pp. 251-259 (English Translation).

Chemical Structural Formulae of the Test Samples (A) Flavan-3-ols (B) Assamicains (C) Theasinensins (D) Theaflavins Chen et al., "Clinical Efficacy of Oolong Tea on Anti-Simple Obesity," Journal of the Japanese Society of Clinical Nutrition, 1998, vol. 20, pp. 83-90 (English translation).
Hashimoto et al., "Tannins and Related Compounds. LVI. Isolation of Four New Acylated Flavan-3-ols from Oolong Tea. (1)," Chem. Pharm. Bull., 1987, vol. 35, No. 2, pp. 611-616.
Hashimoto et al., "Tannins and Related Compounds, XC, 8-C-Ascorbyl (−)-Epigallocatechin 3-O-Gallate and Novel Dimeric Flavan-3-ols, Oolonghomobisflavans A and B, from Oolong Tea," Chem. Pharm. Bull., 1989, vol. 37, No. 12, pp. 3255-3263.
Hashimoto et al., "Tannins and Related Compounds. LXIX. Isolation and Structure Elucidation of $B_3B'$-Linked Bisflavanoids, Theasinensins D-G and Oolongtheanin from Oolong Tea. (2)," Chem. Pharm. Bull., 1988, vol. 36, No. 5, pp. 1676-1684.
Nonaka et al., "Tannins and Related Compounds, XV. A New Class of Dimeric Flavan-3-ol Gallates, Theasinensins A and B, and Proanthocyanidin Gallates from Green Tee Leaf," Chem. Pharm. Bull., 1983, vol. 31, pp. 3906-3914.
Hashimoto et al., "Tannins and Related Compounds, CXIV, Structures of Novel Fermentation Products, Theogallinin, Theaflavonin and Desgalloyl Theaflavonin from Black Tea, and Changes of Tea Leaf Polyphenols during Fermentation," Chem. Pharm. Bull., 1992, vol. 40, No. 6, pp. 1383-1389.
Hashimoto et al., "Tannins and Related Compounds, LXXVII, Novel Chalcan-flavan Dimers, Assamicains A, B and C, and a New Flavan-3-ol and Proanthocyanidins from the Fresh Leaves of Camellia sinensis L., var. Assamica Kitamura," Chem. Pharm. Bull., 1989, vol. 37, No. 1, pp. 77-85.
Hamada et al., "Peroxidase-catalyzed generation of catechin oligomers that inhibit glucosyltransferase from Streptococcus sobrinus," FEMS Microbiology Letters, 1996, vol. 143, pp. 35-40.
European Search Report issued on Oct. 28, 2010 in EP 05765571.4 filed Jul. 5, 2005.
Database WPI Week 200059; Thomson Scientific, London, GB; AN 2000-614836.
Hatano et al., "Theasinensin A, a Tea Polyphenol Formed from (−)-Epigallocatechin Gallate, Suppresses Antibiotic Resistance of Methicillin-Resistant Staphylococcus aureus," Plant Medica, vol. 69, No. 11, Nov. 2003, pp. 984-989.
Saeki et al., "Apoptosis-inducing Activity of Polyphenol Compounds Derived from Tea Catechins in Humans Histiolytic Lymphoma U937 Cells," Biosci. Biotechnol. Biochem., vol. 63, No. 3, Mar. 1999, pp. 585-587.
Nakai et al., "Inhibitory Effects of Oolong Tea Polyphenols on Pancreatic Lipase in Vitro," J. Agric. Food Chem., vol. 53, No. 11, Jun. 2005, pp. 4593-4598.
International Search Report issued on Aug. 16, 2005 in PCT/JP2005/012401 filed Jul. 5, 2005.
Hong et al., Effects of Tea Polyphenols on Arachidonic Acid Metabolism in Human Colon, Chapter 4 in Food Factors in Health Promotion and Disease Prevention, pp. 27-38, ACS Symposium Series, vol. 851, American Chemical Society, Jun. 19, 2003.
Hashimoto et al., Evaluation of the Anti-oxidative Effect (in vitro) of Tea Polyphenols, Biosci. Biotechnol. Biochem., vol. 67, No. 2, pp. 396-401, Feb. 2003.
Kumazawa, Cha Seibun no Seitaimaku ni Taisuru Shinwasei (1), Cha, 2001, vol. 54, No. 2, pp. 36-37 (in Japanese).
Goodman, Barbara "Insights into digestion and absorption of major nutrients in humans," Adv. Physiol Educ., (2010), vol. 34, pp. 44-53.
Shin et al., "Comparison of time course changes in blood glucose, insulin and lipids between high carbohydrate and high fat meals in healthy young women," Nutrition Research and Practice, (2009), vol. 3, No. 2, pp. 128-133.

\* cited by examiner

Primary Examiner — Ernst Arnold
Assistant Examiner — Hong Yu
(74) Attorney, Agent, or Firm — Drinker Biddle & Reath LLP

(57) ABSTRACT

The present invention provides lipase inhibitors containing dimers of flavan-3-ols derived from teas as well as foods and beverages and medicines containing said inhibitors. More specifically, the present invention provides lipase inhibitors containing at least one of assamicains represented by the formula:

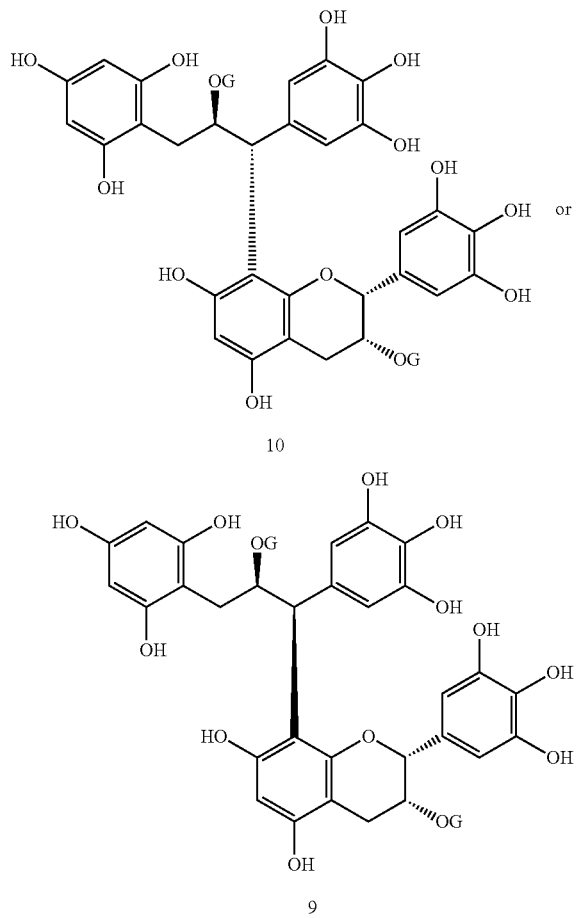

[Formula 1]

wherein G represents a galloyl group;
theasinensins represented by the formula:

[Formula 2]

wherein $R_1$ represents G or H, and $R_2$ represents G; and theaflavins represented by the formula:
[Formula 3]
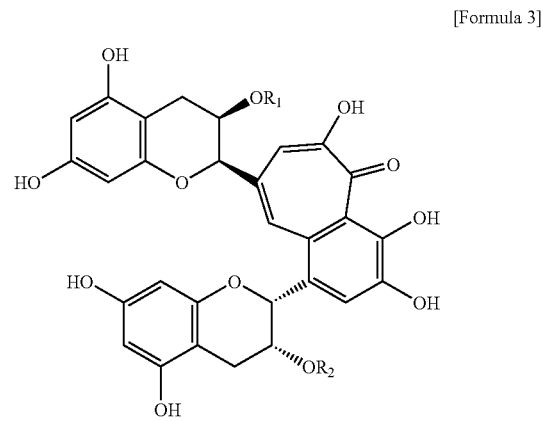
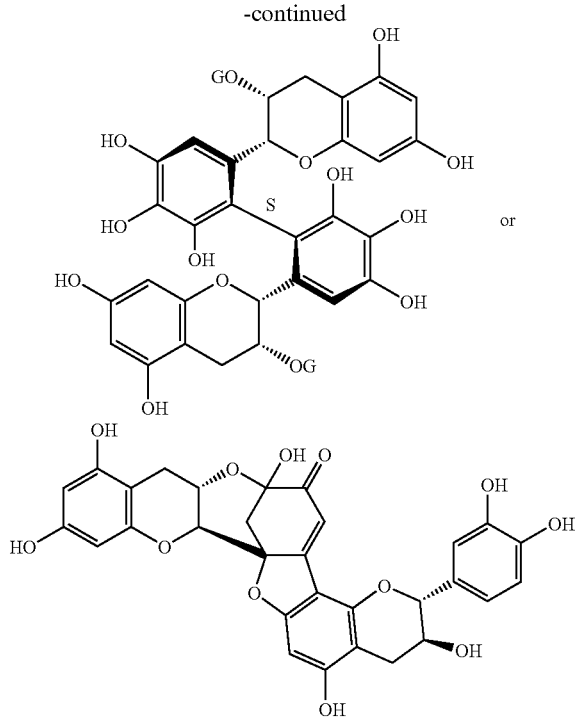
wherein $R_1$ and $R_2$ independently represent G or H; as well as foods and beverages and medicines containing said lipase inhibitors.
6 Claims, 1 Drawing Sheet

Chemical Structural Formulae of the Test Samples
(A) Flavan-3-ols
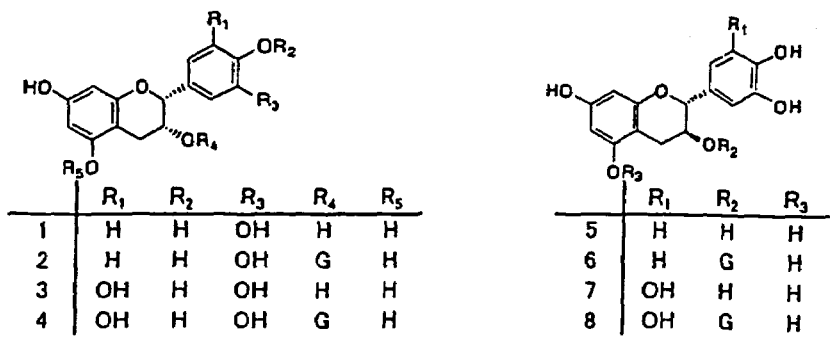
(B) Assamicains
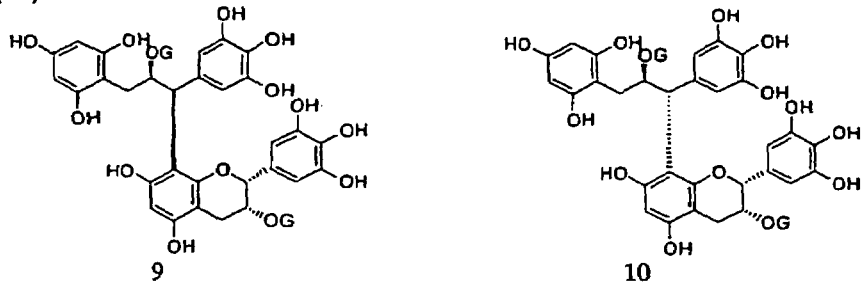
(C) Theasinensins
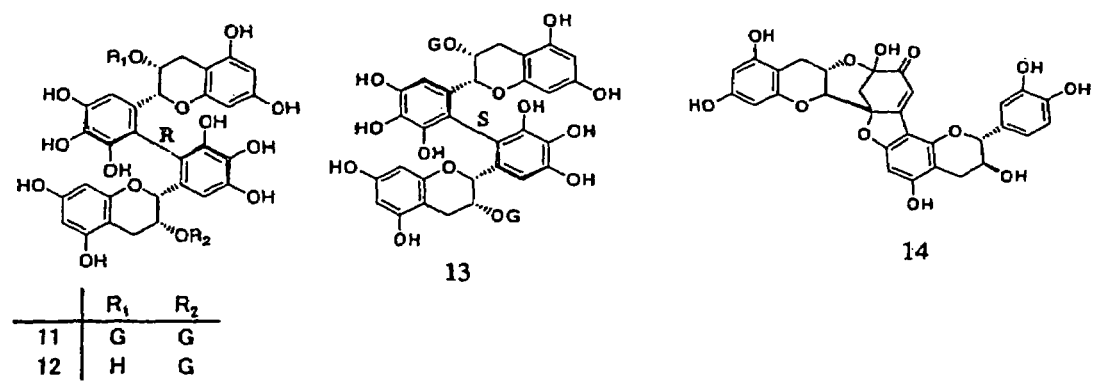
(D) Theaflavins
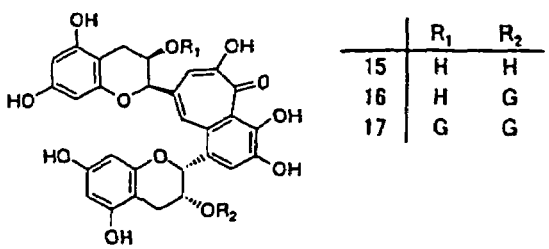

LIPASE INHIBITORS

CROSS REFERENCE TO RELATED APPLICATIONS

This application is a National Stage of International Application No. PCT/JP2005/012401 filed Jul. 5, 2005, and which claims benefit of Japanese Patent Application No. 2004-198342 filed Jul. 5, 2004, which are incorporated by reference herein in their entirety.

TECHNICAL FIELD

The present invention provides lipase inhibitors containing dimers of flavan-3-ols derived from teas.

BACKGROUND ART

In recent years, intake of high-fat foods in Japanese people has been increasing with the increasing westernization of their life style. The 1999 National Nutrition Survey reports that the fat energy ratio exceeds the proper level of 25% despite of the energy intake decreasing year by year and that 50 to 60 percent of the 60 and older population has high triglyceride levels or high cholesterol levels (Ministry of Health, Labor and Welfare of Japan. An overview of the results of the 1999 National Nutrition Survey. Japanese Journal of Clinical Nutrition 2001; 98(5): 577-588).

Obesity is one of the most important diseases in modern society, and mainly caused by excessive consumption of fats. Excessive consumption of fats is known to induce not only obesity but also obesity-associated conditions such as diabetes, hyperlipemia, hypertension and arteriosclerosis. An appetite suppressant Mazindol® is the only drug approved for this obesity in Japan, but it was reported to have adverse side effects such as dry mouth, constipation, stomach discomfort and nausea/vomiting (Clinical Evaluation 1985; 13(2): 419-459; Clinical Evaluation 1985; 13(2): 461-515). Outside Japan, a commercially available drug for improving obesity is Xenical®, which functions to suppress intestinal fat absorption by lipase inhibitory activity, but it is not always safe because it was also reported to have adverse side effects such as fatty stools, increased stool frequency, loose stools, diarrhea and abdominal pain (Lancet 1998; 352: 67-172).

An effective means to prevent obesity is to reduce caloric intake by dietary restrictions, but they should be supervised by an experienced nutrition counselor and it is often difficult to follow them in daily life. Thus, a safe and healthful way to inhibit the absorption of dietary fats by the body would be a practical and useful approach to the treatment of obesity and related diseases or health enhancement.

Against this background, attention has been given to the development of foods for specified health use with proven safety and effectiveness for humans. Foods for specified health use so far marketed as food materials for controlling the increase in serum triglyceride levels after eating include globin digests suppressing fat absorption by pancreatic lipase inhibition (J. Nutr. 1998; 128: 56-60; Journal of the Japanese Society of Nutrition and Food Science 1999; 52(2): 71-77; Journal of Health Food & Nutrition Food Studies 2002; 5(3): 131-144); diacylglycerols having different digestion/absorption characteristics from those of triacylglycerols (J. Am. Coll. Nutr. 2000; 19(6): 789-796; Clin. Chim. Acta. 2001; 11(2): 109-117); and eicosapentaenoic acid (EPA) and docosahexaenoic acid (DHA) purified from fish oils, etc.

Attention is also recently being given to plant-derived materials having lipase inhibitory activity, and especially various polyphenols having lipase inhibitory activity have been reported, such as plant bark-derived tannin (Japanese Patent Publication Sho 60-11912); tannins and flavonoids and glycosides thereof contained in a legume Cassia nomame (Japanese Patent Laying Open Hei 8-259557); food products for inhibiting lipid absorption containing epigallocatechin gallate and epicatechin gallate known as major ingredients in green tea (Japanese Patent Laying Open Hei 3-228664); lipase inhibitors comprising aqueous extracts of green pepper, shimeji mushroom, pumpkin, maitake mushroom, hijiki seaweed, green tea, oolong tea, etc. (Japanese Patent Laying Open Hei 3-219872); flavones and flavonols (Japanese Patent Laying Open Hei 7-61927); hydroxybenzoic acids (gallic acid) (Japanese Patent Laying Open Hei 1-102022); triterpene compounds and derivatives thereof (Japanese Patent Laying Open Hei 9-40689); anti-obesity agents containing procyanidin from tamarind as an active ingredient (Japanese Patent Laying Open Hei 9-291039); as well as lipase inhibitory effects of grape seed extracts (Nutrition 2003; 19(10): 876-879); lipase inhibitory effects and anti-obesity effects in rats of Salacia-derived polyphenols (J. Nutr. 2002; 132: 1819-1824); and anti-obesity effects of oolong tea extracts in mice (Int. J. Obes. 1999; 23: 98-105).

However, plant-derived lipase inhibitors so far reported as shown above are not sufficiently effective. Even if an extract of a plant was effective, for example, it would be difficult to stably maintain lipase inhibitory activity unless the amount of the active ingredient contained in it is specified because it is naturally derived. Moreover, inhibitors derived from tasteless plants have the disadvantage that they affect flavor when they are used as foods or beverages. For example, there are several reports showing the effect of oolong tea in improving lipid profiles by demonstrating a significant decrease in blood triglyceride levels after drinking 1330 ml of commercially available oolong tea daily for 6 weeks (Journal of the Japanese Society of Nutrition and Food Science 1991; 44(4): 251-259) or a weight loss of 1 kg or more in 67% of subjects consisting of 102 men and women with simple obesity who continuously took oolong tea (2 g×4/day) orally for 6 weeks and a significant improving effect after ingestion of oolong tea in subjects showing high blood triglyceride levels (Journal of the Japanese Society of Clinical Nutrition 1998; 20(1): 83-90). Thus, beneficial effects have been observed by drinking plenty of oolong tea, but it is difficult to continue to do so in daily life. If simply concentrated oolong tea was provided, it would not be suitable as a practical means because of strong bitterness/astringency and high caffeine content.

Patent Documents

1. Japanese Patent Publication Sho 60-11912
2. Japanese Patent Laying Open Hei 8-259557
3. Japanese Patent Laying Open Hei 3-228664
4. Japanese Patent Laying Open Hei 3-219872
5. Japanese Patent Laying Open Hei 7-61927
6. Japanese Patent Laying Open Hei 1-102022
7. Japanese Patent Laying Open Hei 9-40689
8. Japanese Patent Laying Open Hei 9-291039

Non-Patent Documents

1. Ministry of Health, Labor and Welfare of Japan. An overview of the results of the 1999 National Nutrition Survey.

2. Japanese Journal of Clinical Nutrition 2001; 98(5): 577-588.
3. Clinical Evaluation 1985; 13(2): 419-459. Clinical Evaluation 1985; 13(2): 461-515.
4. Lancet 1998; 352: 67-172.
5. J. Nutr. 1998; 128: 56-60.
6. Journal of the Japanese Society of Nutrition and Food Science 1999; 52(2): 71-77.
7. Journal of Health Food & Nutrition Food Studies 2002; 5(3): 131-144.
8. J. Am. Coll. Nutr. 2000; 19(6): 789-796.
9. Clin. Chim. Acta. 2001; 1.1 (2): 109-117.
10. Nutrition 2003; 19(10): 876-879.
11. J. Nutr. 2002; 132: 1819-1824.
12. Int. J. Obes. 1999; 23: 98-105.
13. Journal of the Japanese Society of Nutrition and Food Science 1991; 44(4): 251-259.
14. Journal of the Japanese Society of Clinical Nutrition 1998; 20(1): 83-90.
15. Chem. Pharm. Bull 1987; 35(2): 611-616.
16. Chem. Pharm. Bull 1989; 37(12): 3255-3563.
17. Chem. Pharm. Bull. 1988; 36(5): 1676-1684.
18. Chem. Pharm. Bull. 1983; 31(11): 3906-3914.
19. Chem. Pharm. Bull. 1992; 40(6): 1383-1389.
20. Chem. Pharm. Bull. 1989; 37(1): 77-85.
21. FEMS Microbiol. Lett. 1996; 143: 35-40.

DISCLOSURE OF THE INVENTION

Problem to be Solved by the Invention

The present invention focuses on ingredients contained in highly tasty teas and provides lipase inhibitors containing at least one of dimers of flavan-3-ols derived from teas.

The present invention also provides highly tasty foods and beverages containing said lipase inhibitors for reducing blood triglycerides and for enhancing health.

The present invention also provides pharmaceutical compositions containing said lipase inhibitors for inhibiting absorption of dietary fats to prevent an increase in blood triglycerides.

Means for Solving Problem

As a means for solving the above problems, we found tea-derived ingredients inhibiting pancreatic lipase essential for fat absorption, and evaluated the lipase inhibitory activity of various polyphenols present therein, and ascertained that dimers of flavan-3-ols have strong lipase inhibitory activity.

More specifically, lipase inhibitors of the present invention are characterized in that they contain at least one of dimers of flavan-3-ols selected from the group consisting of assamicains represented by the formula:

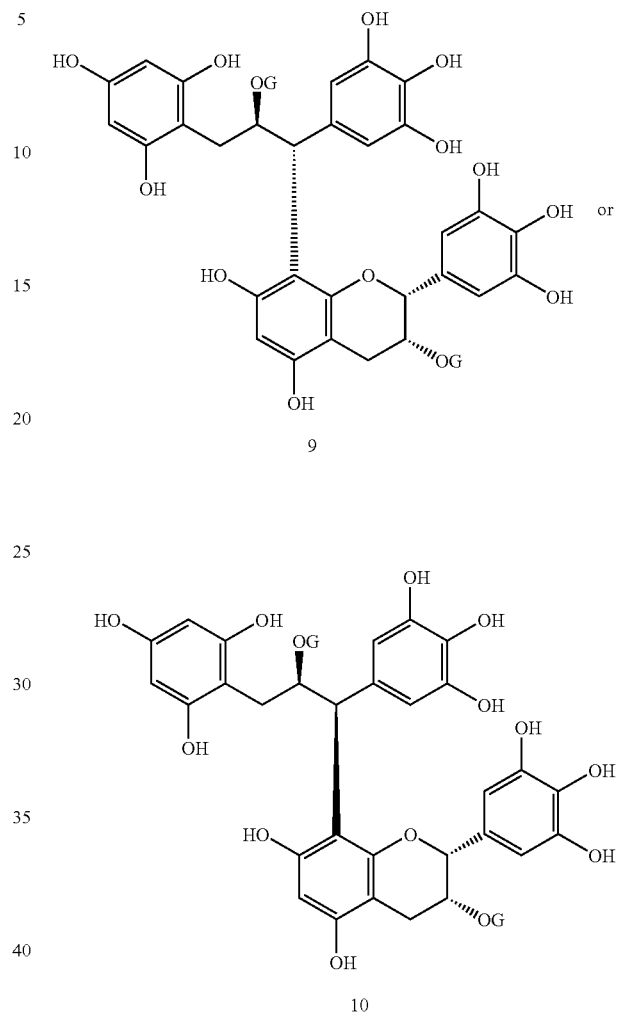

[Formula 1]

wherein G represents a galloyl group;
theasinensins represented by the formula:

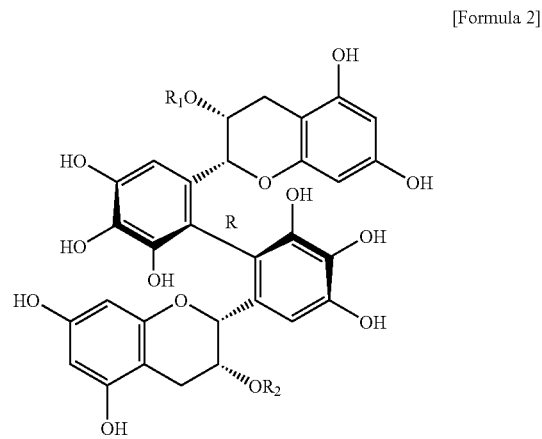

[Formula 2]

-continued

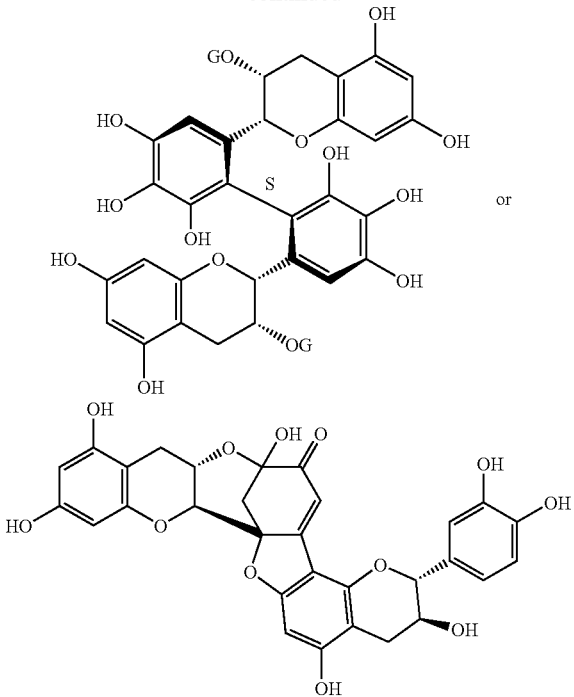

wherein R₁ represents G or H, and R₂ represents G; and theaflavins represented by the formula:

[Formula 3]

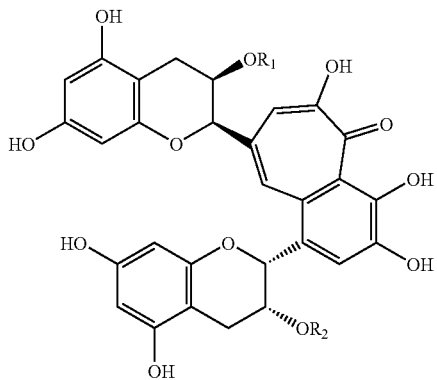

wherein R₁ and R₂ independently represent G or H.
The galloyl group G has the structural formula:

[Formula 4]

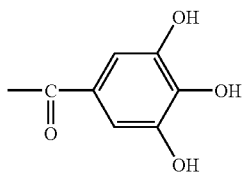

Examples of assamicains contained in lipase inhibitors of the present invention include assamicain A (compound 9) and assamicain B (compound 10).

Examples of theasinensins contained in lipase inhibitors of the present invention include theasinensin A (compound II), theasinensin B (compound 12), theasinensin D (compound 13) and dehydro-dicatechin A (compound 14).

Examples of theaflavins contained in lipase inhibitors of the present invention include theaflavin (compound 15), theaflavin 3'-O-gallate (compound 16) and theaflavin 3,3'-di-O-gallate (compound 17).

Dimers of flavan-3-ols of the present invention are commercially available or can be obtained by extraction from natural materials such as commercially available green tea, black tea and oolong tea. For example, purification of diols of flavan-3-ols from oolong tea leaves is reported in Chem. Pharm. Bull. 1987; 35(2): 611-616; Chem. Pharm. Bull. 1988; 36(5): 1676-1684; Chem. Pharm. Bull. 1983; 31(11): 3906-3914; Chem. Pharm. Bull. 1992; 40(6): 1383-1389; Chem. Pharm. Bull. 1989; 37(12): 3255-3563; or Chem. Pharm. Bull. 1989; 37(1): 77-85. Dehydro-dicatechin A can be obtained by the process described in FEMS Microbiol. Lett. 1996; 143: 35-40, as described in Example 2 below.

Lipase Inhibitors

Dimers of flavan-3-ols of the present invention can be used alone as lipase inhibitors without including other components, or can be used as lipase inhibitors in combination with solvents or solid carriers. The solvents or carriers are preferably those capable of being safely used as foods or medicines in terms of the uses for foods and beverages and/or medicines as described below. Lipase inhibitors of the present invention have various uses such as experimental and research purposes or uses as active ingredients of foods and medicines for preventing accumulation of triglycerides.

Method for Assaying Lipase Inhibitory Activity

Lipase inhibitors of the present invention have a strong inhibitory effect against lipases, especially pancreatic lipase. The inhibitory activity can be assayed by the method specifically described in Example 1.

Foods and Beverages Containing Lipase Inhibitors

Lipase inhibitors containing dimers of flavan-3-ols of the present invention can be added as active ingredients for inhibiting lipase to foods and beverages to prevent an undesirable increase in blood triglycerides associated with intake of dietary fats and/or reduce increased blood triglycerides. Preferred examples of foods and beverages include those consumed on a daily basis such as green tea, barley tea, oolong tea, black tea, coffee, isotonic drink, drinking water, seasonings, and dressings. However, the foods and beverages may be those commonly consumed such as soft drinks, cocktails, beer, whiskey, distilled spirits, wine, sake, seasonings, dressings, flavored rice, processed foods, convenience foods, retort foods, chocolates, fresh cream, cakes, dairy products, health foods and supplements.

Lipase inhibitors of the present invention are added to foods and beverages in an amount corresponding to an intake of dimers of flavan-3-ols of 0.1 mg to 10 g per meal. However, there is no substantial upper limit on the amount of dimers of flavan-3-ols of the present invention that can be added to foods and beverages because they are derived from foods and therefore very safe.

Medicines Containing Lipase Inhibitors

Lipase inhibitors containing dimers of flavan-3-ols of the present invention can also be used as active ingredients of drugs for inhibiting absorption of dietary fats and preventing and/or reducing an undesirable increase of blood triglycerides. Preferred drugs are those orally administered, such as drinkable preparations, tablets, capsules, granules, powders, candies and hard candies. The amount of dimers of flavan-3-ols of the present invention is 0.1 mg to 10 g per dose.

Medicines of the present invention are safely taken even for a long period because of high safety of lipase inhibitor ingredients. Therefore, they can be taken even on a daily basis to prevent or correct obesity as a lifestyle-related disease.

Effect of the Invention

The present invention can provide highly tasty foods and beverages containing a lipase inhibitor including at least one of dimers of flavan-3-ols derived from tea leaves for reducing triglycerides and for enhancing health without compromising flavor. Beverages enriched with tea-derived active ingredients are very significant because the inhibitor should desirably be taken with meals in order to inhibit absorption of dietary fats. Especially, the present invention made it possible to develop drinks for preventing obesity and enhancing health by enriching them with these ingredients.

BRIEF EXPLANATION OF THE DRAWINGS

FIG. 1 shows the chemical structural formulae of the compounds evaluated for lipase inhibitory activity in Example 3.

EXAMPLES

Examples 1

Lipase Inhibitory Activity Assay

A lipase activity assay was performed by using the oleate ester of fluorescent 4-methylumbelliferone (4-MUO) as a substrate to measure the fluorescence of 4-methylumbelliferone produced by reaction.

The buffer used for the assay was 13 mM Tris-HCl (pH 8.0) containing 150 mM NaCl, 1.36 mM $CaCl_2$. The enzyme assay was performed using a 0.1 M solution of the substrate 4-MUO (Sigma) in DMSO diluted 1:1000 in said buffer and a solution of porcine pancreatic lipase (Sigma) prepared at 400 U/ml also in said buffer.

An enzymatic reaction was started by adding 25 μl of the lipase/buffer solution after 50 μl of the 4-MUO/buffer solution and 25 μl of distilled water (or an aqueous solution of each sample) were added and mixed in a 96-well microplate at 25° C. After the reaction was performed for 30 minutes, the reaction was stopped by adding 100 μl of a 0.1 M citrate buffer (pH 4.2) and the fluorescence of 4-methylumbelliferone produced by the reaction (excitation 355 nm, emission 460 nm) was measured using a fluorescence plate reader (Fluoroskan Asent CF from Labsystems).

The inhibitory activity of each test sample was determined as $IC_{50}$(μM), i.e. the amount of the sample giving 50% inhibition of the activity of the control (distilled water).

Test Samples

Catechin (C), epicatechin (EC), gallocatechin (GC), epigallocatechin (EGC), catechin gallate (CG), epicatechin gallate (ECG), gallocatechin gallate (GCG) and epigallocatechin gallate (EGCG) were purchased from Wako Pure Chemical Industries, Ltd.

Among dimers of catechins, dehydro-dicatechin A was synthesized with a tea leaf enzyme. The procedure is shown in Example 2.

The other compounds were obtained by the processes described in the following articles: Chem. Pharm. Bull. 1987; 35(2): 611-616; Chem. Pharm. Bull. 1988; 36(5): 1676-1684; Chem. Pharm. Bull. 1983; 31(11): 3906-3914; Chem. Pharm. Bull. 1992; 40(6): 1383-1389; Chem. Pharm. Bull. 1989; 37(12): 3255-3563; and Chem. Pharm. Bull. 1989; 37(1): 77-85. Briefly, oolong tea leaves were extracted with 80% acetone, after which acetone was removed and the extract was fractionated with water, methanol and 50% acetone on Sephadex LH-20 (Pharmacia). Each fraction was purified on MCI-gel CHP-20P (Mitsubishi Kasei Corp.) and Fuji gel ODS-G3 (Fuji Silysia Chemical Ltd.)

Example 2

Synthesis of Dehydro-Dicatechin A

Tea leaves of Kyoken No. 129 variety (supplied from Kyoto Prefectural Tea Research Institute) (100 g) were ground in liquid nitrogen and stirred with 600 ml of an extraction buffer (adjusted to pH 7.0 with 0.01 M $KH_2PO_4$ and 0.02 M $K_2HPO_4$) and 100 ml of polyamide, and then filtered through gauze. The filtrate was centrifuged at 8000 rpm for 20 min. The supernatant (500 ml) was stirred with 500 ml of acetone precooled to −20° C., and then the mixture was allowed to stand at 4° C. for 1 hr. This solution was centrifuged at 8000 rpm, 4° C. for 20 min to give a white precipitate. This precipitate was dissolved in 100 ml of a reaction buffer (adjusted to pH 5.6 with 0.01 M citrate and 0.02 M $KH_2PO_4$) to prepare an enzymatic solution.

To 100 ml of the enzymatic solution were added 100 mg of D-(+)-catechin and 8.8 mM $H_2O_2$ and allowed to stand at 32° C. After 5 hrs, the reaction was stopped by adding 100 ml of 90% acetonitrile containing 1% TFA. This solution was diluted 1:5 in water and applied onto HP-20 (200 ml, Mitsubishi Kasei Corp.) and washed with water, after which the reaction product was eluted with 400 ml of 90% acetonitrile containing 0.1% TFA and concentrated under reduced pressure, and then lyophilized. The reaction product was purified by preparative HPLC as follows:

Column: Develosil C30-UG-5 (20 mmφ×250 mm, Nomura Chemical Co., Ltd.)

Mobile phase: (A) 0.1% TFA/$H_2O$, (B) 90% $CH_3CN$, 0.1% TFA

Detection: A280 nm

Flow rate: 6 ml/min

Gradient: Linear gradient elution from B20% to B70% for 40 min.

This chromatography gave dehydro-dicatechin A at an elution time of 21 min (for reference, see FEMS Microbiol. Lett. 143 35-40, 1996).

Example 3

Lipase Inhibitory Activity of Catechins and Dimers Thereof

Catechins (monomers) and dimeric compounds produced by polymerization of catechins known as major polyphenols in teas were assayed for lipase inhibitory activity according to the method of Example 1. The results are shown in Table 1. The chemical structural formulae of the compounds subjected to evaluation are shown in FIG. 1. Among major catechins (8 catechins) present in teas, flavan-3-ols having a gallate moiety bonded via an ester linkage showed lipase inhibitory activity. Especially, epigallocatechin gallate (EGCG) abundantly found in teas showed the strongest activity among the major catechins.

Among dimeric polyphenols, those having a gallate group in their structure, especially dimers of EGCG were shown to have higher lipase inhibitory activity than EGCG per se.

[Table 1]

TABLE 1

| Lipase inhibitory activity of tea-derived polyphenols | |
|---|---|
| Polyphenols | IC$_{50}$ (μM) |
| Flavan-3-ols | |
| (−)-epicatechin (1) | >21.6 |
| (−)-epicatechin 3-O-gallate (2) | 0.271 |
| (−)-epigallocatechin (3) | >20.4 |
| (−)-epigallocatechin 3-O-gallate (4) | 0.284 |
| (+)-catechin (5) | >690 |
| (−)-catechin 3-O-gallate (6) | 0.846 |
| (+)-gallocatechin (7) | >163 |
| (−)-gallocatechin 3-O-gallate (8) | 0.349 |
| Assamicains | |
| assamicain A (9) | 0.120 |
| assamicain B (10) | 0.186 |
| Theasinensins | |
| theasinensin A (11) | 0.142 |
| theasinensin B (12) | 0.276 |
| theasinensin D (13) | 0.098 |
| dehydro-dicatechin A (14) | 3.090 |
| Theaflavins | |
| theaflavin (15) | 0.106 |
| theaflavin 3'-O-gallate (16) | 0.112 |
| theaflavin 3,3'-di-O-gallate (17) | 0.092 |

It was shown from the above results that dimers having very high activity also exist in teas in addition to the major catechins (8 catechins).

The invention claimed is:

1. A method for treating postprandial hypertriglyceridemia comprising administering to a mammal in need thereof a composition containing at least one of the compounds selected from the group consisting of theaflavin, theaflavin 3'-O-gallate and theaflavin 3,3'-di-O-gallate, wherein postprandial hypertriglyceridemia is treated with the composition.

2. The method of claim 1, wherein the composition is administered with a meal, and wherein the composition suppresses absorption of dietary triglycerides and/or suppresses a rise of triglycerides in blood associated with intake of dietary triglycerides.

3. The method of claim 1, wherein the composition comprises at least theaflavin 3,3'-di-O-gallate.

4. The method of claim 2, wherein the composition comprises at least theaflavin 3,3'-di-O-gallate.

5. The method of claim 1, wherein the composition consists essentially of one or more of the compounds selected from the group consisting of theaflavin, theaflavin 3'-O-gallate and theaflavin 3,3'-di-O-gallate.

6. The method of claim 2, wherein the composition consists essentially of one or more of the compounds selected from the group consisting of theaflavin, theaflavin 3'-O-gallate and theaflavin 3,3'-di-O-gallate.

* * * * *